United States Patent [19]

Jyoko

[11] Patent Number: 5,134,665
[45] Date of Patent: Jul. 28, 1992

[54] APPARATUS AND METHOD OF INSPECTING SOLDER PRINTING

[75] Inventor: Nobuhiro Jyoko, Kanagawa, Japan

[73] Assignee: Mitsubishi Denki Kabushiki Kaisha, Japan

[21] Appl. No.: 655,055

[22] Filed: Feb. 14, 1991

[30] Foreign Application Priority Data

Mar. 8, 1990 [JP] Japan ................. 2-56883

[51] Int. Cl.⁵ .............................. G06K 9/00
[52] U.S. Cl. .......................... 382/8; 382/34; 358/101; 358/107
[58] Field of Search ............. 382/8, 34; 358/101, 358/106, 107; 304/513

[56] References Cited

U.S. PATENT DOCUMENTS

| | | | |
|---|---|---|---|
| 4,233,625 | 11/1980 | Altman | 382/8 |
| 4,441,205 | 4/1984 | Berkin et al. | 382/8 |
| 4,668,982 | 5/1987 | Tinnerino | 358/101 |
| 4,731,853 | 3/1988 | Hata et al. | 358/101 |
| 4,852,131 | 7/1989 | Armistead | 382/8 |
| 4,922,434 | 5/1990 | Fule | 358/101 |

FOREIGN PATENT DOCUMENTS 99286 4/1989 Japan .

OTHER PUBLICATIONS

Ikegamitsushin K.K. Model No. MS 400R (No Date).
TDK Model No. CE-1500 (No Date).
Fuji Model No. GSPII-400 (No Date).
Nyurongu Seimitsu K.K. Model No. LS 34 TVA (No Date).
Kyushu Matsushita Electric Co., Ltd. Model No. SP10P-L (No Date).
Matsushita Electric Industrial Co., Ltd. Model No. NM-2624 (No Date).

Primary Examiner—Leo H. Boudreau
Attorney, Agent, or Firm—Wolf, Greenfield & Sacks

[57] ABSTRACT

A displacement sensor is attached to the XY direction movable body adapted to move over the land pattern of a printed circuit board in an X direction and Y direction, and rotatable in a direction parallel to the printed circuit board. The rotary mechanism allows the displacement sensor to be rotated in a direction which is orthogonal to the movement direction of XY direction movable body. The signals from said displacement sensor will be processed so that the film thickness and the print pattern of the solder on the land pattern may be detected. An ITV area sensor is also provided at said XY direction movable body so that the signals from the ITV area sensor may be processed to detect any print deviation of the soldering deviation on said land pattern.

6 Claims, 6 Drawing Sheets

PRIOR ART　　PRIOR ART

PARALLEL SCANNING　　ORTHOGONAL SCANNING

PRIOR ART　　PRIOR ART (0° ROTATION)  (90° ROTATION)

$X1 - X2 = \Delta X'$ $\dfrac{(y1-y2)+(y3-y4)}{2} = \Delta y'$

APPARATUS AND METHOD OF INSPECTING SOLDER PRINTING

BACKGROUND OF THE INVENTION

1. Field of the Invention

The present invention relates to an apparatus and a method of inspecting solder printing and more particularly to an apparatus and a method of measuring the print deviation, the film thickness and the print pattern of the solder which has been supplied on the land pattern for attaching the components of a printed circuit board for surface mounting of the electronic components on a printed circuit board.

2. Description of Prior Art

The inspection apparatus for solder print according to a prior art is illustrated in FIG. 1.

In FIG. 1, numeral 1 designates a printed circuit board, numeral 2 a land pattern for mounting components, numeral 3 a paste-like solder supplied on the land pattern 2, numeral 5 a reference bore for positioning the printed circuit board 1, numeral 6 a positioning pin, numeral 7 a laser type displacement sensor, numeral 8 an orthogonal XY axes robot adapted to drive the laser type displacement sensor 7 in the X and Y directions, and numeral 9 a processing circuit adapted to process the signals from the laser type displacement sensor 7. The laser type displacement sensor 7 is fixedly mounted to the orthogonal XY axes robot 8.

Operation of the solder printing inspection apparatus as described above will next be explained.

The printed circuit diagram with the paste-like solder initially supplied to a part of the land pattern 2 is set on the jig 4. Then, the orthogonal XY axes robot 8 activates a scanning operation by the measuring point of the laser type displacement sensor 7 which then scans from the portion of the land pattern 2 to which the paste-like solder 3 has not been applied to the portion of the land pattern 2 to which the solder has been applied. The processing circuit 9 is adapted, upon reception of the signals from the laser type displacement sensor 7 which has thus scanned the land portion, to detect the height at the respective measuring points of the respective portions of the land pattern as described above. Since the positions of both portions having respectively been applied and not applied with the paste-like solder are detected in terms of height at the sampling points of the land pattern, the thickness of the film of the paste-like solder may be measured by searching the difference of height between the portions supplied with the solder and not applied with the same. According to the illustrated embodiment, since the surface of a part of the land pattern not supplied with the paste-like solder 3 is used as the reference surface for measuring the thickness of the film of the solder, an accurate film thickness measurement is made possible.

In this way, insertion of the positioning pin 6 of the jig 4 into the reference bore 5 of the printed circuit board 1 makes it possible to measure the film thickness of the paste-like solder 3.

The principle of measurement of the film thickness by the laser type displacement sensor 7 will next be described in connection with FIG. 2.

As shown in FIG. 2, the laser type displacement sensor 7 comprises an optical position sensing element 7a, a light reception lens 7b, a semiconductor laser 7c and a light projection lens 7d. The processing circuit 9 adapted to process the signals from the laser type displacement sensor 7 comprises an A/D converter 9a, a computing control section 9b and an input/output interface 9c. Measurement of displacement is carried out in such a way that a laser beam is irradiated on the surface of the portion of the land pattern to be measured and a portion of the diffused light emitted from the surface is then sensed by the optical position sensing element 7a. If the irradiated portion of the beam be displaced from the object A in FIG. 2 (the surface of the land pattern 2 serving as the reference) to the position B (the height of the paste-like solder 3 supplied on the land pattern 2), the beam spot on the optical position sensing element 7a will be moved in accordance with trigonometry. The amount of displacement is converted to an electric signal and the computing control section 9b computes the amount of displacement based on the electric signal. This amount of displacement or the thickness of the solder film may be obtained by subtracting the height B of the paste-like solder from the height A of the land pattern 2 serving as the reference for the laser type displacement sensor 7 in the following equation.

$$h = A - B$$

However, since the surface of the paste-like solder has a considerable undulation, the height displacement may be obtained by approximating the displacements at the respective sampling positions scanned by the laser type displacement sensor 7.

In the meantime as shown in FIGS. 3(a) and 4(a), the relationship between the scanning direction of the laser type displacement sensor 7 as moved by the orthogonal XY axes robot [i.e., X directions in FIGS. 3(a) and 4(a)] and the linear direction connecting the semiconductor laser 7c and the optical position sensing element 7a of the laser type displacement sensor 7 (referred hereinafter called as "light projection and light reception directions") is found both in the parallel scanning in which the light projection and light reception direction are in parallel with the scanning direction (X direction) and the orthogonal scanning in which the light projection and light reception direction are orthogonal to the scanning direction (X direction). In the case of the parallel scanning, the displacement of the steps (or edge portion) between the land pattern 2 and the paste-like solder 3 cannot be accurately measured as shown in FIG. 3(b) due to the influence by the light projection and the light reception regarding the laser beam. In order to cope with this problem, in the example shown in FIG. 1, the laser type displacement sensor 7 is fixed on the plane parallel to the printed circuit board so that the directions of light projection and light reception may be oriented in a Y scanning direction orthogonal to the X scanning direction (or the moving direction of the orthogonal XY axes robot 8) so as to allow an accurate measurement to be made when the laser type displacement sensor 7 is scanned in an X direction.

According to the solder printing inspection apparatus according to a prior art as explained above, since the laser type displacement sensor 7 is fixed to the orthogonal XY axes robot 8, scanning in one direction (X direction) in an orthogonal scanning operation is only available for measurement, so that accurate measurement of the film thickness and the print pattern cannot be expected. Besides, print deviation cannot be measured, so that such a measurement has to be done by way of a visual inspection.

SUMMARY OF THE INVENTION

Accordingly, the present invention has been proposed to solve the problems as described above and an object of the present invention is to provide a solder printing inspection apparatus and method capable of measuring with a high degree of accuracy the film thickness and the print pattern of the solder as well as the print deviation.

In the solder printing inspection apparatus according to the present invention, an ITV area sensor adapted to detect the print deviation of the solder applied on the land pattern of a printed circuit diagram is attached to the XY direction movable body of the orthogonal XY axes robot and a displacement sensor adapted to measure by scanning the film thickness and the print pattern of the solder supplied on the land pattern of a printed circuit board is attached rotatably to the XY direction movable body by means of a rotary mechanism whereby the rotary mechanism is so controlled as to enable the displacement sensor always to be oriented in a constant direction relative to the moving direction of the XY direction movable body. In this way, the print deviation of the paste-like solder supplied on the land pattern of a printed circuit diagram may be measured by the ITV area sensor. In addition, the laser type displacement sensor is oriented by the rotary mechanism in an orthogonal direction to the moving direction of the orthogonal XY axes robot so that the film thickness and the print pattern of the paste-like solder supplied on the land pattern may be measured.

BRIEF DESCRIPTION OF THE DRAWINGS

The present invention may be better understood by referring to the accompanying drawings wherein.

DESCRIPTION OF A PREFERRED EMBODIMENT

Figure 1:
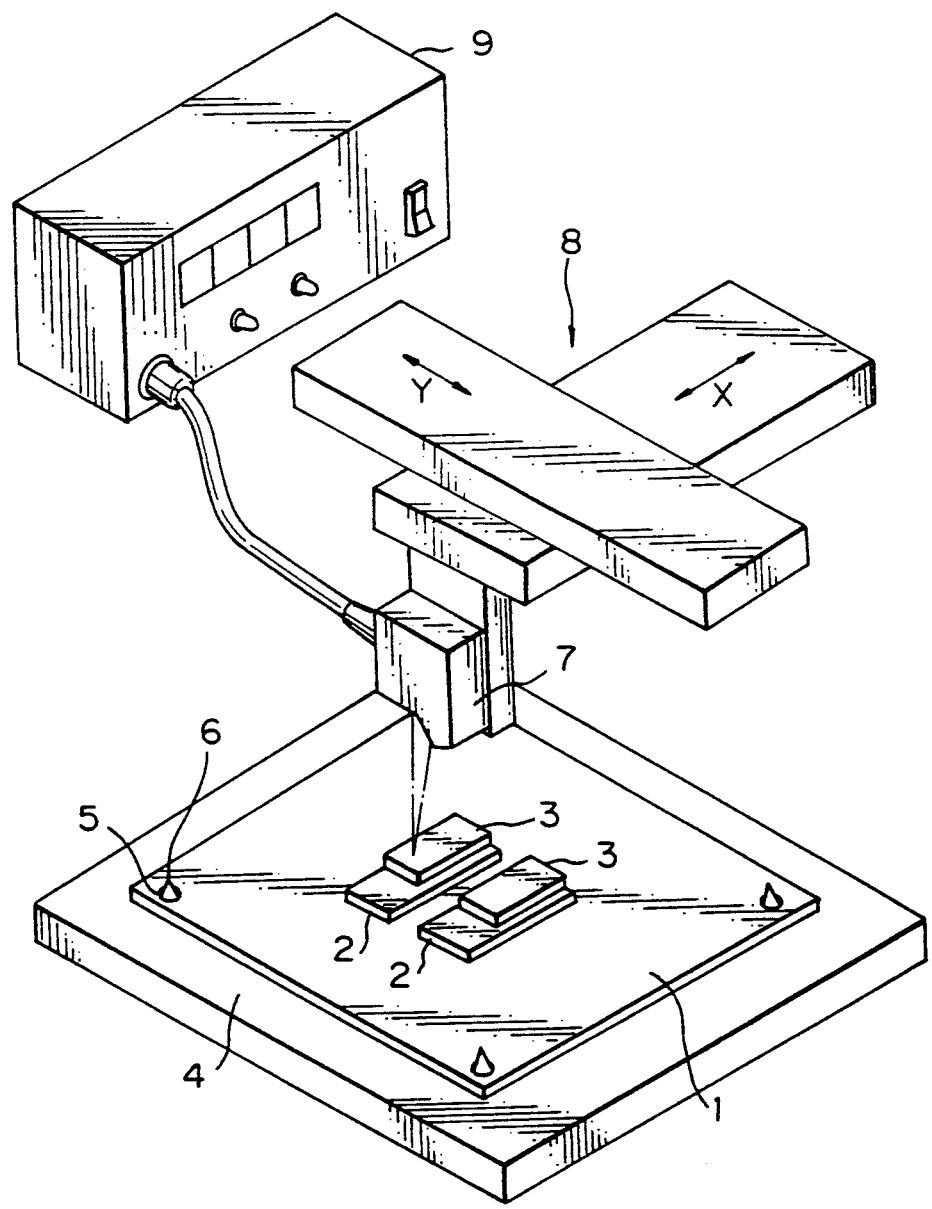
FIG. 1 illustrates a overall constitution of the solder printing inspection apparatus according to a prior art.
Figure 2:
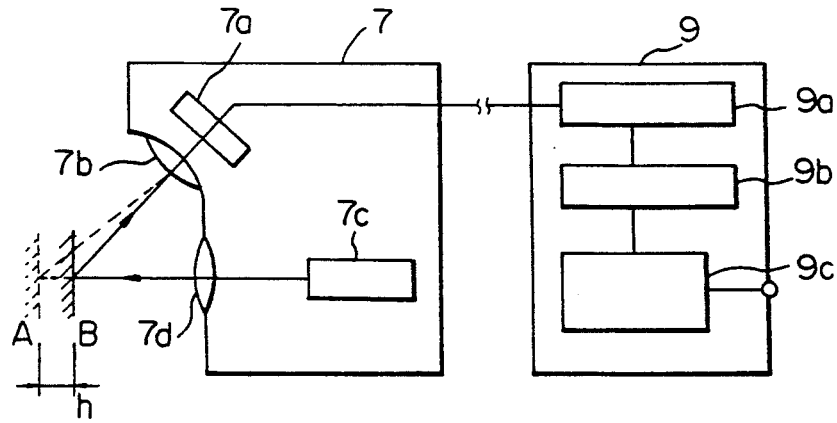
FIG. 2 illustrates a principle of measurement by use of a laser type displacement sensor.
Figures 3A, 4A:
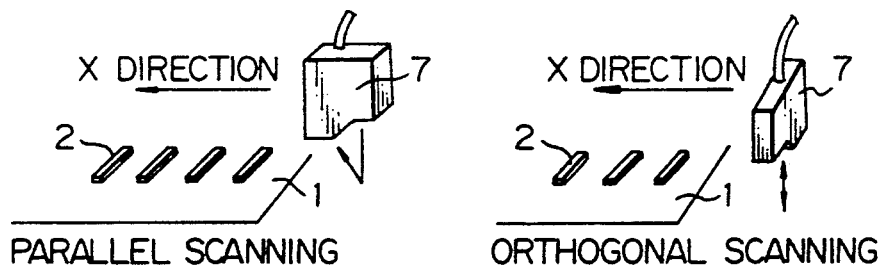
FIGS. 3(a), 3(b), 4(a) and 4(b) illustrate the method of scanning by a laser type displacement sensor and the scanning data.
Figures 3B, 4B:
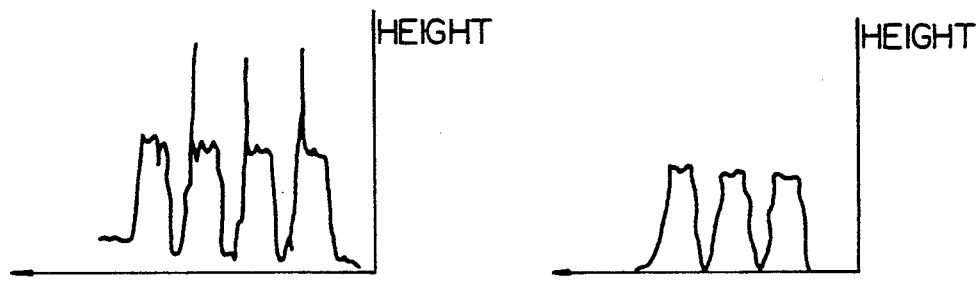

An embodiment of the present invention will now be explained by referring to FIG. 5 through FIG. 9. Those components identical to those of a prior art shown in FIGS. 1 and 2 are designated by the identical symbols and the explanation thereof is not repeated.

Figure 5:
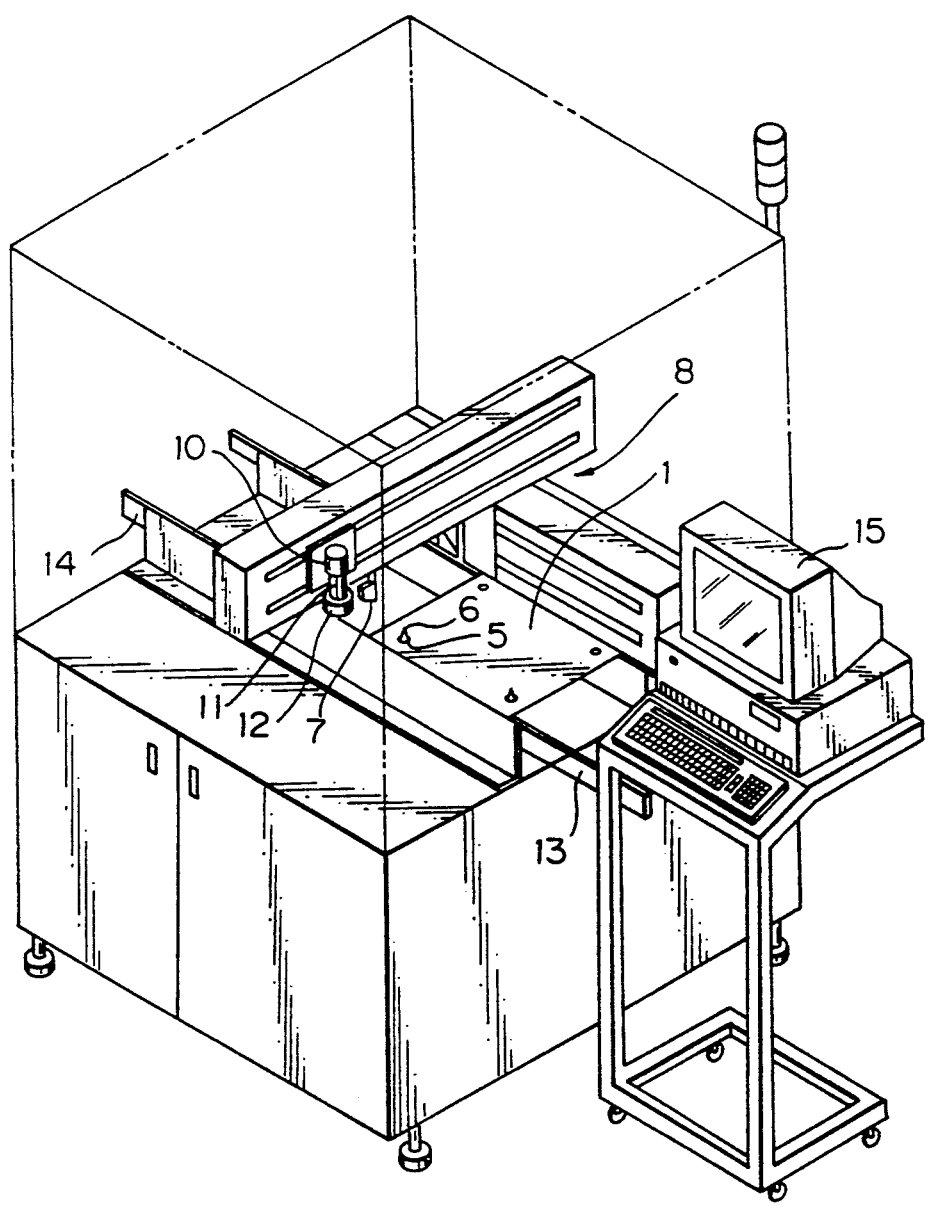
FIG. 5 illustrates a overall constitution of the solder printing inspection apparatus according to the present invention.
Figure 6A:
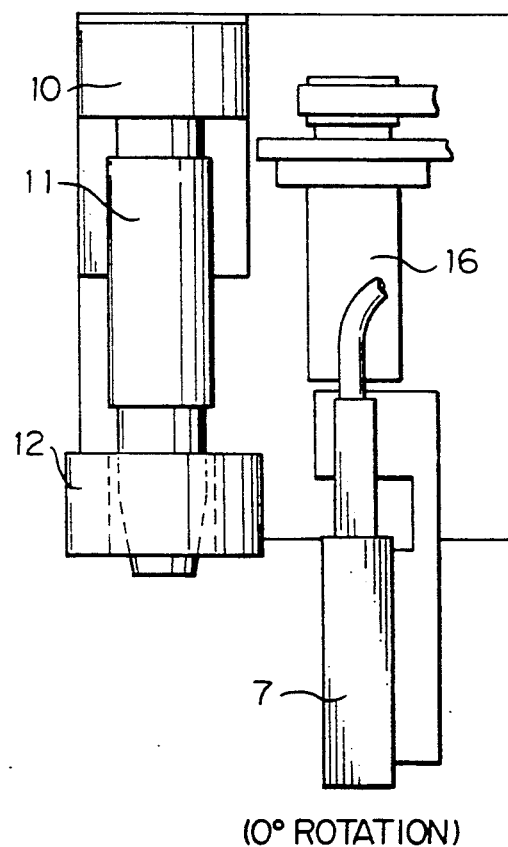
FIGS. 6(a) and 6(b) are fragmentary enlarged views of the solder printing inspection apparatus shown in FIG. 5.
Figure 6B:
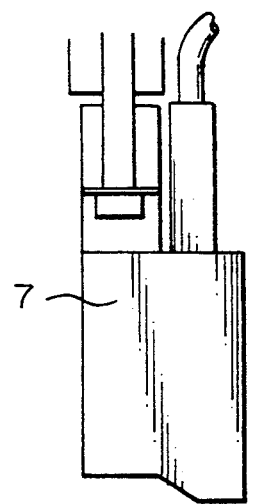

FIG. 5 is a simplified perspective view illustrating the constitution of the solder printing inspection apparatus according to the present invention. FIGS. 6(a) and (b) are fragmentary enlarged views. In the respective drawings, numeral 10 designates an ITV camera, numeral 11 a lens barrel, numeral 12 a ring illumination, numeral 13 a feeding conveyor for a printed circuit board 1, numeral 14 a delivery conveyor for delivering a printed circuit board 1 after inspection, numeral 15 a computer as the processing circuit and numeral 16 a rotary mechanism for the laser type displacement sensor 7.

Operation of the inspection apparatus as described above will next be explained.

The printed circuit board 1 with the paste-like solder 3 applied on the land pattern 2 is transferred to the inspection area by the feed conveyor 13. At the inspection area, the positioning pin 6 is inserted through the reference bore 5 of the printed circuit board to position the circuit board 1.

Figure 7:
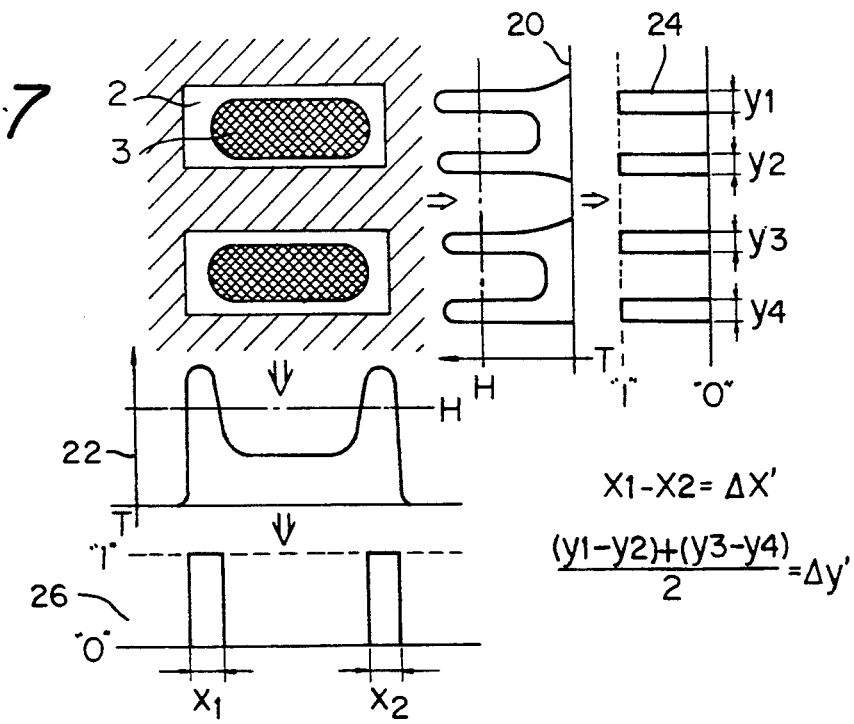
FIGS. 7, 8 and 9 illustrate the method of measuring the print deviation.
Figure 8:
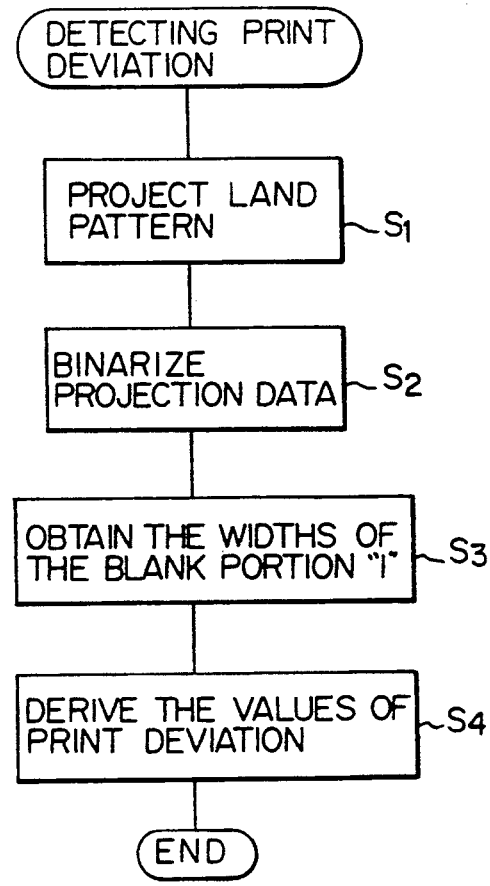
Figure 9:
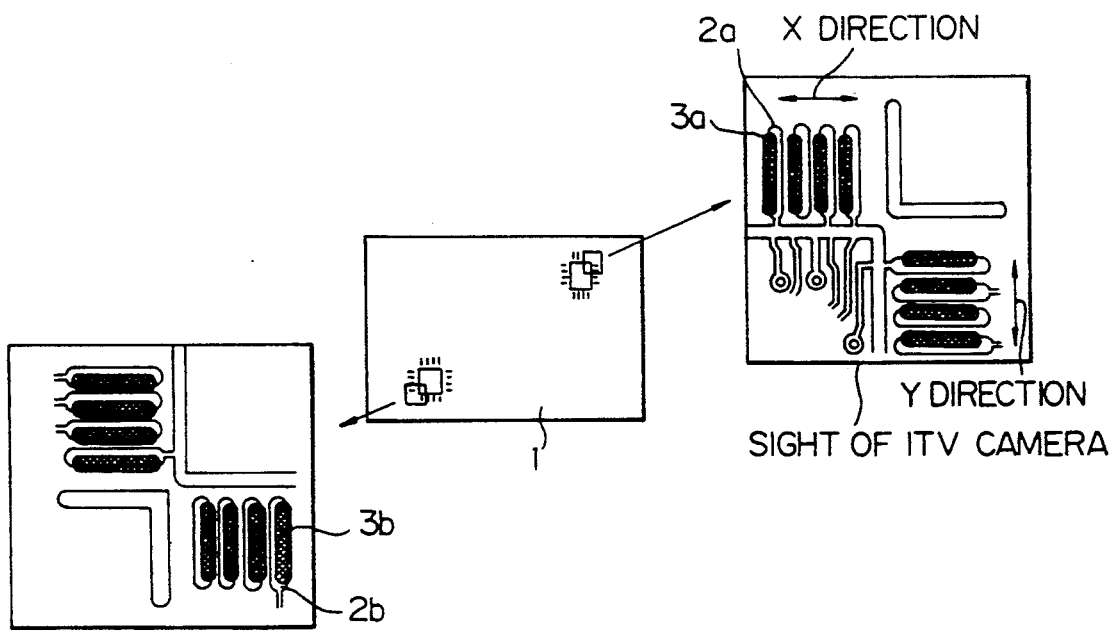

The print deviation of the paste-like solder 3 supplied on the land pattern 2 is measured by using the ITV camera 10 in the manner as shown in FIGS. 7 and 8, the ITV camera being attached to the orthogonal XY axes robot 8 in a manner as to be driven over the plane parallel to the printed circuit board 1. Measurement of the value of deviation is performed at two locations on the printed circuit board which are sufficiently spaced from each other as shown in FIG. 9.

At each location, the ITV sensor or camera provides a signal indicative of light intensity as illustrated by reference numerals 20 and 22, (FIG. 7), for the Y direction and X direction respectively. Thus, the projection of land pattern 2 is obtained. (Step $S_1$ of FIG. 8). This projection data thus obtained is binarized by using a certain value (or threshold value H)(step $S_2$ in FIG. 8). As illustrated by reference numerals 24 and 26 (FIG. 7) for the Y direction and X direction respectively. Then the widths $x_1$, $x_2$ of the portions (blank portion "1") of the land pattern in the X direction to which the paste-like solder has not been applied are obtained and the widths $y_1$, $y_2$, $y_3$, $y_4$ of the portions (blank portion "1") of the land pattern in the Y direction to which the paste-like solder has not been applied are obtained (Step $S_3$ in FIG. 8). Next, the value $\Delta x'$ of deviation in the X direction is derived from the following equation (1) and the value $\Delta y'$ of deviation in the Y direction is derived from the equation (2) (Step $S_4$ in FIG. 8).

$$x_1 - x_2 = \Delta x' \tag{1}$$

$$\frac{(y_1 - y_2) + (y_3 - y_4)}{2} = \Delta y' \tag{2}$$

Figure 10:
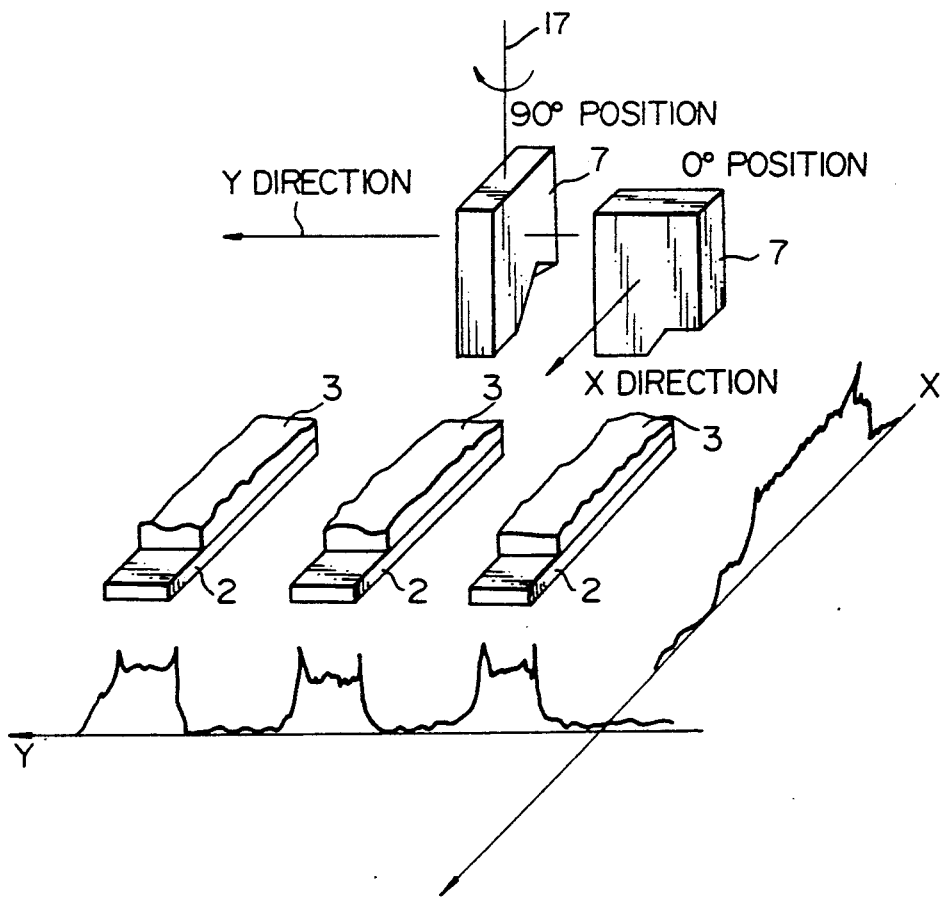
FIG. 10 illustrates the method of measuring the film thickness and the print pattern.

Measurement of the film thickness and the print pattern of the solder is executed by using the laser type displacement sensor 7 attached to the orthogonal XY axes robot 8 and in a manner as shown in FIG. 10. In order to measure the film thickness, the laser type displacement sensor 7 is located at its 0° position as shown in FIG. 10 and caused to scan in the X direction. In this way, the thickness is measured by deducting the height of the land pattern 2 which is the reference height from the height of the paste-like solder 3 thus scanned. At this time, since the laser type displacement sensor 7 is oriented in the Y direction, i.e. the light projection and reception direction of the sensor is the Y direction, which is orthogonal to the X scanning direction (or the direction of the movement of the orthogonal XY axes robot 8) so that orthogonal scanning is performed, thus providing an accurate measurement. At the time of measurement of a print pattern, the laser type displacement sensor 7 is rotated by the rotary mechanism 16 about an axis 17 perpendicular to the plane of the printed circuit board, to its 90° position shown in FIG.

10 and caused to scan in the Y direction. Also, on this occasion, the laser type displacement sensor 7 is oriented in the X scanning direction orthogonal to the Y direction (or the movement direction of the orthogonal XY axes robot 8) to provide orthogonal scanning whereby an accurate measurement may be provided. This permits any print pattern including the deviation of solder printing and so forth to be measured.

According to the constitution as described above, since the laser type displacement sensor 7 is oriented by the rotary mechanism 16 in such a manner that the direction of light projection and light reception is directed to be orthogonal to the movement direction of the orthogonal XY axes robot 8 and caused to scan under this condition, orthogonal scanning by the orthogonal XY axes robot 8 may be executed in both the X and Y directions, the film thickness and the print pattern of the paste-like solder 3 applied on the land pattern 2 may be accurately measured. Furthermore, since ITV camera 10 is attached to the orthogonal XY axes robot 8, any print deviation may be accurately measured.

It is to be noted that in the above-described embodiment the invention apparatus is designed to be an independent paste-like solder printing inspection apparatus but it may be incorporated in an aggregate solder printing inspection apparatus.

The above-described apparatus is capable of not only detecting any defective print by measuring the print deviation, the film thickness and the print pattern of the solder after it has been printed, but also of feeding back the printing position to be compensated and the printing conditions to the solder printing inspection apparatus so as to provide a print of higher quality.

As explained above, the present invention makes it possible to measure the film thickness and the print pattern of the solder applied on the land pattern of a printed circuit board to be measured with high accuracy as well as the print direction of the printed solder to be measured with high accuracy.

Having now described a particular embodiment of the present invention, it should now become apparent to those skilled in the art that numerous other embodiments and the modifications are contemplated as falling within the scope of the present invention, as defined by the appended claims.

What is claimed is:

1. A solder printing inspection apparatus comprising:
   a body;
   means for moving the body in at least a first direction and a second direction perpendicular to the first direction, whereby the body can move over the land pattern of a printed circuit board;
   a displacement sensor rotatably attached to said body having a direction of scanning, and providing signals indicative of the distance between the sensor and the printed circuit board;
   a rotary mechanism for rotating said displacement sensor about an axis substantially perpendicular to said printed circuit board so that the direction of scanning is orthogonal to the direction of movement of said body;
   a first means for processing the signals from said displacement sensor so as to obtain the film thickness and the printing pattern of the solder on said land pattern;
   an ITV area sensor attached to said body and providing signals indicative of the printing pattern on the land pattern; and
   a second means for processing the signals from said ITV area sensor so as to detect print deviation of The solder on said land pattern.

2. A method of solder printing inspection, for inspecting a pattern of solder printing on a land pattern of a printed circuit board, comprising the steps of:
   acquiring projection data of the land pattern of the printed circuit board and the pattern of printed solder on said land pattern using an ITV sensor;
   converting said projection data into binary values by using a predetermined threshold value;
   calculating a width of portions of the land pattern without solder from said binary values;
   calculating an amount of print deviation of the solder on the land pattern from said width;
   moving a rotable displacement sensor, having a scanning direction, in a moving direction over the printed circuit board, maintaining the scanning direction substantially orthogonal to the moving direction, thereby obtaining a distance between the sensor and the printed circuit board; and
   calculating the thickness and pattern of the solder on said land pattern from said distance.

3. A solder printing inspection apparatus for inspecting a printed circuit board, comprising:
   a body;
   means for moving the body in a plane parallel to the printed circuit board;
   a displacement sensor rotatably attached to the body for scanning the land pattern of the printed circuit board and having means for providing a signal indicative of the distance between the sensor and the printed circuit board,
   a first means for processing the signal provided by said displacement sensor having means for providing a signal indicative of the thickness and pattern of solder on said printed circuit board,
   an ITV sensor for projecting an image of a land pattern on a printed circuit board and having means for providing a signal indicative of projection of the land pattern on the printed circuit board, and
   a second means for processing the signals from the ITV sensor having means for detecting print deviation of the solder on the land pattern.

4. A solder printing inspection apparatus as set forth in claim 3, wherein said means for moving includes first means for moving said body in a first direction and second means for moving said body in a second direction perpendicular to said first direction.

5. A method as set forth in claim 2, further comprising the steps of:
   detecting any defective print on the printed circuit on the basis of said calculated print deviation, film thickness and print pattern.

6. A method as set forth in claim 2, further comprising the steps of:
   providing the calculated print deviation and the calculated thickness and pattern of solder on the land pattern to the printing apparatus to compensate for detected defective printing.

* * * * *